United States Patent [19]

Stroetmann et al.

[11] Patent Number: 5,554,179
[45] Date of Patent: Sep. 10, 1996

[54] IMPLANTABLE DIFIBRILLATOR ELECTRODE

[75] Inventors: Brigitte Stroetmann, Uttenreuth; Gerhard Starbeck, Nuremberg, both of Germany

[73] Assignee: Pacesetter AB, Sweden

[21] Appl. No.: 268,893

[22] Filed: Jun. 30, 1994

[30]    Foreign Application Priority Data

Jul. 2, 1993  [DE]  Germany ............... 43 22 130.0

[51] Int. Cl.⁶ ........................................ A61N 1/05
[52] U.S. Cl. ............................ 607/129; 607/121
[58] Field of Search ....................... 607/152, 115, 607/116, 129, 131; 128/640, 639, 641, 642

[56]    References Cited

U.S. PATENT DOCUMENTS

| | | | |
|---|---|---|---|
| 4,352,359 | 10/1982 | Larimore et al. | 128/640 |
| 5,143,089 | 9/1992 | Alt . | |
| 5,154,182 | 10/1992 | Moaddeb | 607/129 |
| 5,269,810 | 12/1993 | Hull et al. | 607/129 |

FOREIGN PATENT DOCUMENTS

0475027A1  3/1992  European Pat. Off. .

*Primary Examiner*—William E. Kamm
*Assistant Examiner*—Scott M. Getzow
*Attorney, Agent, or Firm*—Kenyon & Kenyon

[57]    ABSTRACT

In an implantable defibrillator electrode having a large surfaced electrode in the form of a netting, a spiral, or a fabric of electronically conductive material or having an intracardial electrode in the form of a coil of electronically conductive material, the electrode is completely embedded in a biocompatible, hydrophilic, electrolytically conductive polymer or is covered by such a polymer.

17 Claims, 1 Drawing Sheet

IMPLANTABLE DIFIBRILLATOR ELECTRODE

BACKGROUND OF THE INVENTION

1. Field of the Invention

The present invention relates to an implantable defibrillator having a large surfaced electrode in the form of a netting, a spiral, or a fabric of electronically conductive material,or having an intracardinal electrode in the form of a coil of electronically conductive material, as well as a method of producing such a defibrillator.

2. Description of Related Art

The purpose of defibrillators is to detect and treat abnormal heart rates, i.e. disturbances in rhythm and arrhythmias (see, for instance, EP-OS 0 475 027). The detection of disturbances of rhythm is effected, for instance, via myocardial screw electrodes. They detect a ventricular flutter or fibrillation by, for instance, measuring the heart rate or by recording an electrocardiogram (ECG). Upon the recognition of ventricular fluttering or fibrillation an electric shock is given off after a few seconds. The current pulse is impressed on the heart by large surfaced electrodes (patches) and/or by intracardial electrodes (see, for instance, German OS 39 14 662).

As the mechanism of action of the electric defibrillation there is assumed a synchronous irritation of all non-refractory myocardial regions. It is therefore necessary for the entire myocardial symplast to be excited simultaneously. This, however, presupposes sufficient current density.

The electrodes of defibrillators must be flexible so that they can adapt themselves to the physiological conditions of the body and the heart. Furthermore, they must be biocompatible and their surface should not irritate the surrounding tissue by additional rubbing. Resistance to corrosion, low polarization, and long-term stability are further important criteria which must be satisfied by such electrodes.

Up to now, large surfaced electrodes for defibrillators have consisted of metal nettings or spirals which are embedded on one side into a layer of silicone rubber and are contacted on the other side. While the nettings, in general, consist of titanium, the spirals consist of platinum. Between the electrically conductive netting or spiral and the surrounding tissue there is direct contact, which—due to the roughness of the metal—can lead to rubbing of the tissue. Intracardial electrodes can consists of non-metallic, electrically conductive fibers.

SUMMARY OF THE INVENTION

Figure 1:
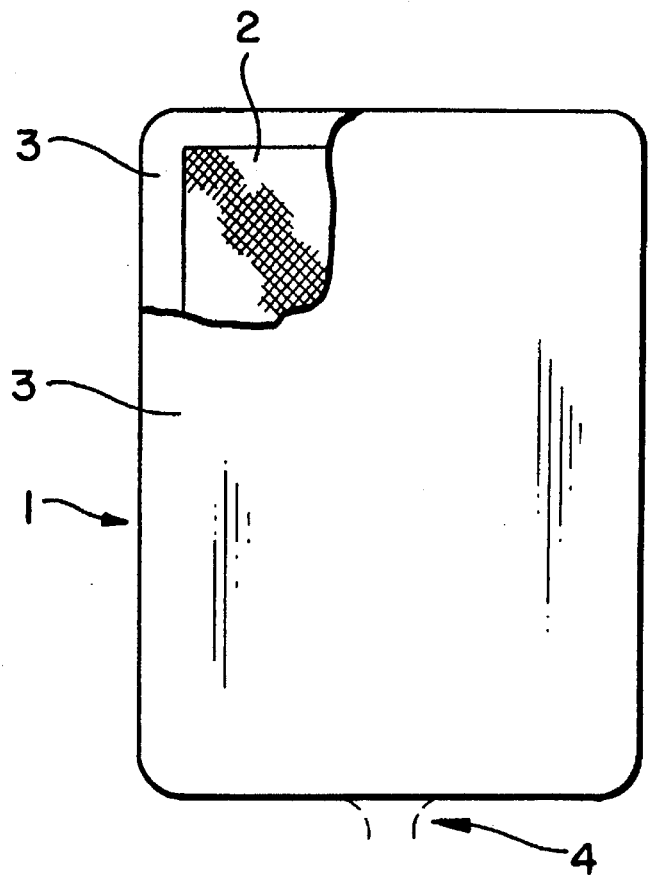
FIG. 1 describes a perspective view of the implantable defibrillator electrode of the present invention.
Figure 2:
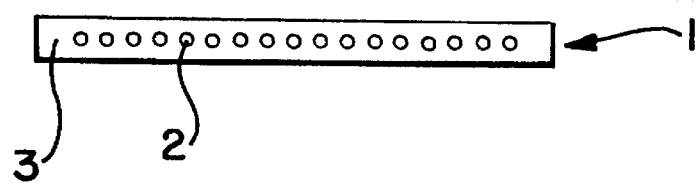
FIG. 2 describes a cross section of the implantable defibrillator electrode of the present invention. (1) denotes the electrode; (2) denotes an electronically conductive netting; (3) denotes the polymer membrane. The electrode is coupled to a power source at (4).

The object of the invention is to further improve implantable defibrillators having a large surfaced electrode or an intracardial electrode of the aforementioned type,with respect to the their fitness and capability for use.

This is achieved in accordance with the invention by providing an electrode which is completely embedded in a biocompatible, hydrophilic, electrolytically conductive polymer or is surrounded by such a polymer.

DETAILED DESCRIPTION OF THE INVENTION

In the implantable defibrillator of the invention, the special construction of the electrode avoids having the electronic conductor be in direct contact with the tissue. In addition, since the polymer, due to its hydrophilic character, swells slightly upon contact with the body fluid, the transition between the conductive structure and the body tissue produces only slight rubbing (i.e., a "cushioning effect").

In contradistinction to the silicone which has been previously used and which has an insulating action, an electrolytically conductive polymer is used in the defibrillator of the invention. This is of great advantage particularly if external defibrillation is necessary due to failure of the (internal) defibrillator system. In this case, the external defibrillation can be effected with small amounts of energy. In addition, there is the further advantage that the tissue is not unnecessarily acted on by high energy.

The polymer is, in general, an ion exchanger. In addition to anion exchangers, cation exchangers are advantageously used, preferably in the form of poly(perfluoroalkylene-)sulfonic acids particularly sulfonated polytetrafluoroethylene. This has the advantage that the surface of the electrode is kept free of negatively charged macromolecules. As a result, the removal of the electrode after a given period of implantation is simpler. Another example of a suitable cation exchanger is a sulfonated copolymer of styrene and divinyl benzene. Instead of sulfonic acid groups, the cation exchangers can, for instance, also have carboxylic acid or phosphoric acid groups.

The thickness of the large surfaced electrode is preferably ≦300 μm. In this way, a high flexibility is assured. Platinum or platinum/iridium is preferably used as material for the large surfaced electrode and for the intracardial electrode Furthermore titanium, for instance, can also be used as electrode material. In the case of large surfaced electrodes, the electrode material can advantageously also be conductive carbon. For this purpose, there are used, in particular, fabrics of conductive carbon, for instance in the form of a netting of carbon fiber bundles.

For the production of the electrode for the implantable defibrillator of the invention, an electronically conductive netting or a corresponding spiral can be covered in a suitable manner with a polymer. However, a netting or spiral of electronically conductive material may be arranged between two membranes of a biocompatible, hydrophilic, electrolytically conductive polymer and this arrangement compressed at elevated temperature and pressure and the netting or spiral then contacted.

Using such a procedure, the result is that the polymer adheres firmly on the netting or spiral and, at the same time, the necessary mechanical stability is assured. Furthermore, the two membranes—together with the netting or spiral—are so pressed together that they do not loosen from each other during the defibrillator shock, which involves a strong development of gas.

Fabrics of conductive carbon and coils of electronically conductive material can be provided with a polymer covering, for instance in the form of a tube. The covering can also be formed by treating said materials with a polymer solution, for instance immersed in such a solution.

An anti-inflammatory steroid can advantageously be incorporated in the polymer. For this purpose, the electrode provided with the polymer can be treated with a suspension containing polymer and steroid.

After contacting the electrode produced in the manner described is combined with a suitable electronic system and thus results in a defibrillator which is suitable for implantation.

The invention will be further described below with reference to the following exemplary embodiment which should be regarded in an illustrative rather than a restrictive sense.

EXAMPLE

A 0.06 mm thick platinum netting (mesh width: 0.25 mm) of a size of 50 mm×80 mm is arranged between two commercial membranes, each of a thickness of about 180 µm, of sulfonated polytetrafluoroethylene in $F^-$ form (Nafion$^R$ 117). This arrangement (total thickness: about 420 µm) is placed between two tempered niobium sheets, each of a thickness of 0.15 mm, so as to prevent adherence of the membranes to the press surface upon the pressing. For the pressing, the entire arrangement is introduced into an 0.3 mm thick metal frame and compressed for 10 minutes at a pressure of about 30 bar and a temperature of about 230° C. Thereupon, cooling to a temperature of 25° C. is effected within 8 minutes. The electrodes removed from the press have a thickness of about 300 µm.

In order to convert the $F^-$ form of the polymer, i.e. the ion-exchanger material, into the $H^+$ form, hydrolysis and conditioning are carried out in known manner. For this purpose, the electrode is first treated for about 6 hours with a mixture of a 2.5 molar sodium hydroxide solution and ethanol (in a ratio of 5:1) at a temperature of 65° C. Thereupon, the electrode is removed from the solution and washed neutral with water. The electrode is then immersed for 30 minutes in boiling water and then stored for 16 hours at room temperature in 1.5-normal sulfuric acid. The electrode is then again washed neutral with water, again immersed for 30 minutes in boiling water, and then cooled.

What is claimed is:

1. An implantable defibrillator electrode comprising a large surfaced electrode in the form of a netting, a spiral, or a fabric of electronically conductive material, the electrode being embedded completely in a biocompatible, hydrophilic, electrolytically conductive polymer.

2. The implantable defibrillator electrode according to claim 1 wherein the electrode has a thickness ≦300 µm.

3. The implantable defibrillator electrode according to claim 2 wherein the electrode consists of conductive carbon.

4. An implantable defibrillator electrode according to claim 2 wherein the electrode consists of platinum or platinum and iridium.

5. An implantable defibrillator electrode according to claim 2 wherein the polymer is a cation exchanger.

6. An implantable defibrillator electrode according to claim 5 wherein the cation exchanger is poly(perfluoroalkylene)sulfonic acid.

7. An implantable defibrillator electrode according to claim 2 wherein a steroid is incorporated in the polymer.

8. The implantable defibrillator electrode according to claim 1 wherein the electrode consists of conductive carbon.

9. An implantable defibrillator electrode according to claim 1 wherein the electrode consists of platinum or platinum and iridium.

10. An implantable defibrillator electrode according to claim 1 wherein the polymer is a cation exchanger.

11. An implantable defibrillator electrode according to claim 10 wherein the cation exchanger is poly(perfluoroalkylene)sulfonic acid.

12. An implantable defibrillator electrode according to claim 1 wherein a steroid is incorporated in the polymer.

13. An implantable defibrillator electrode comprising an intracardial electrode in the form of a coil of electronically conductive material, the electrode being covered completely by a biocompatible, hydrophilic, electrolytically conductive polymer.

14. An implantable defibrillator electrode according to claim 13 wherein the electrode consists of platinum or platinum and iridium.

15. An implantable defibrillator electrode according to claim 13 wherein the polymer is a cation exchanger.

16. An implantable defibrillator electrode according to claim 15 the cation exchanger is poly(perfluoroalkylene) sulfonic acid.

17. An implantable defibrillator electrode according to a claim 13 wherein a steroid is incorporated in the polymer.

* * * * *